(12) United States Patent
Wich

(10) Patent No.: US 6,605,058 B1
(45) Date of Patent: Aug. 12, 2003

(54) DEVICE FOR INTRODUCING A NEEDLE

(75) Inventor: Horst Wich, Cathedral City, CA (US)

(73) Assignee: Disetronic Licensing AG, Burgdorf (CH)

(*) Notice: Subject to any disclaimer, the term of this patent is extended or adjusted under 35 U.S.C. 154(b) by 0 days.

(21) Appl. No.: 09/581,589

(22) PCT Filed: Nov. 17, 1997

(86) PCT No.: PCT/CH97/00434
§ 371 (c)(1),
(2), (4) Date: Oct. 27, 2000

(87) PCT Pub. No.: WO99/25400
PCT Pub. Date: May 27, 1999

(51) Int. Cl.$^7$ ................................................ A61M 5/32
(52) U.S. Cl. ...................................... 604/117; 604/412
(58) Field of Search ................................. 604/257, 181, 604/187, 196, 117, 411, 412

(56) References Cited

U.S. PATENT DOCUMENTS

| 2,531,267 A | 11/1950 | Harnisch ............... 128/218 |
| 2,664,086 A | 12/1953 | Transue ............... 128/218 |
| 3,605,744 A | 9/1971 | Dwyer ............... 128/218 F |
| 3,677,245 A | 7/1972 | Welch ............... 128/218 S |
| 4,445,510 A | 5/1984 | Rigby ............... 128/329 R |
| 4,735,611 A | 4/1988 | Anderson et al. ............ 604/130 |
| 4,946,446 A | 8/1990 | Vadher ............... 604/198 |
| 4,973,318 A | 11/1990 | Holm et al. ............... 604/208 |
| 5,092,842 A | 3/1992 | Bechtold et al. ............. 604/135 |
| 5,114,406 A | 5/1992 | Gabriel et al. ............... 604/136 |
| 5,209,739 A | 5/1993 | Talalay ............... 604/195 |
| 5,244,465 A | 9/1993 | Michel ............... 604/218 |
| 5,292,314 A | 3/1994 | D'Alessio et al. ........... 604/198 |
| 5,338,311 A | 8/1994 | Mahurkar ............... 604/195 |
| 5,514,097 A | 5/1996 | Knauer ............... 604/136 |
| 5,527,294 A | 6/1996 | Weatherford et al. ........ 604/198 |
| 5,540,664 A | 7/1996 | Wyrick ............... 604/136 |
| 5,549,558 A | 8/1996 | Martin ............... 604/110 |
| 5,573,510 A | 11/1996 | Isaacson ............... 604/158 |
| 5,643,214 A | 7/1997 | Marshall et al. ............ 604/134 |
| 5,658,259 A | 8/1997 | Pearson et al. ............. 604/232 |
| 5,779,677 A | 7/1998 | Frezza ............... 604/134 |
| 5,873,856 A | 2/1999 | Hjertman et al. ........... 604/117 |

FOREIGN PATENT DOCUMENTS

| AU | 5861273 | 1/1975 |
| DE | 1491841 | 7/1969 |
| DE | 3638984 | 5/1988 |
| DE | 3645245 | 1/1994 |
| EP | 0268191 | 5/1988 |
| EP | 0516473 | 12/1992 |
| EP | 0518416 | 12/1992 |
| FR | 2700960 | 8/1994 |
| WO | WO9110460 | 7/1991 |
| WO | WO9305835 | 4/1993 |
| WO | WO9409841 | 5/1994 |
| WO | WO9501812 | 1/1995 |
| WO | WO9927986 | 6/1999 |

*Primary Examiner*—Edward K. Look
*Assistant Examiner*—Michael Leslie
(74) *Attorney, Agent, or Firm*—Dorsey & Whitney LLP

(57) ABSTRACT

A device for introducing a needle for injecting a liquid substance, wherein the device includes a housing, a rear longitudinal part forming a portion of the housing and including a piercing needle, the rear longitudinal part being connectable to an injection device separate from the housing, a front longitudinal part forming another portion of the housing and including an injection needle for delivering said liquid, and a flexible connection between the piercing needle and the injection needle.

22 Claims, 3 Drawing Sheets

DEVICE FOR INTRODUCING A NEEDLE

This application claims the priority of PCT application number PCT/CH97/00434, filed Nov. 17, 1997, which is incorporated herein by reference.

BACKGROUND

The invention relates to a device for introducing a needle for injecting a liquid substance. With conventional injection devices known, there is often the problem that the user himself is unable to introduce the injection needle into the tissue skin or subcutaneously and is dependent on assistance or a trained person.

SUMMARY OF THE INVENTION

The object of the present invention is to provide a device for introducing a needle which makes it possible to relieve the user of having to introduce the injection needle into the tissue skin or subcutaneously, and which permits administration of the individualized dose by means of the conventional injection device.

The invention achieves this object by providing a device for introducing a needle comprising a rear longitudinal part including a piercing needle, the rear longitudinal part being connectable to a conventional injection device; a frontal longitudinal part including an injection needle for delivering said liquid substance into the tissue skin or subcutaneously; and a flexible connection between said piercing needle and said injection needle.

Serving as the control element is an initiator sleeve arranged longitudinally shiftable on a piercing needle mount, mounting the piercing needle, and cooperates with an injection needle mount, mounting the injection needle, and likewise longitudinally shiftable in a stopper sleeve.

Introducing the injection needle into the tissue skin or subcutaneously after manual activation of the initiator sleeve occurs in that the injection needle mount together with the injection needle is moved by means of the force of a spring automatically in the direction of the tissue skin. Following automatic introduction of the injection needle in the tissue skin or subcutaneously, the user is able to administer the dose of liquid substance required by means of the conventional injection device.

The device for introducing a needle in accordance with the invention has the salient advantage that it can be coupled to any commercially available, conventional injection device, that it offers highly reliable assurance in controlling the introduction depth of the injection needle into the tissue skin or subcutaneously, and that this device for introducing a needle has a relatively simple configuration and, thus, is reasonably priced.

Further advantageous aspects of the invention read from the sub-claims.

BRIEF DESCRIPTION OF THE DRAWINGS

An example embodiment of the invention is illustrated in the Figures in which.

DETAILED DESCRIPTION OF THE PREFERRED EMBODIMENTS

Figure 1:
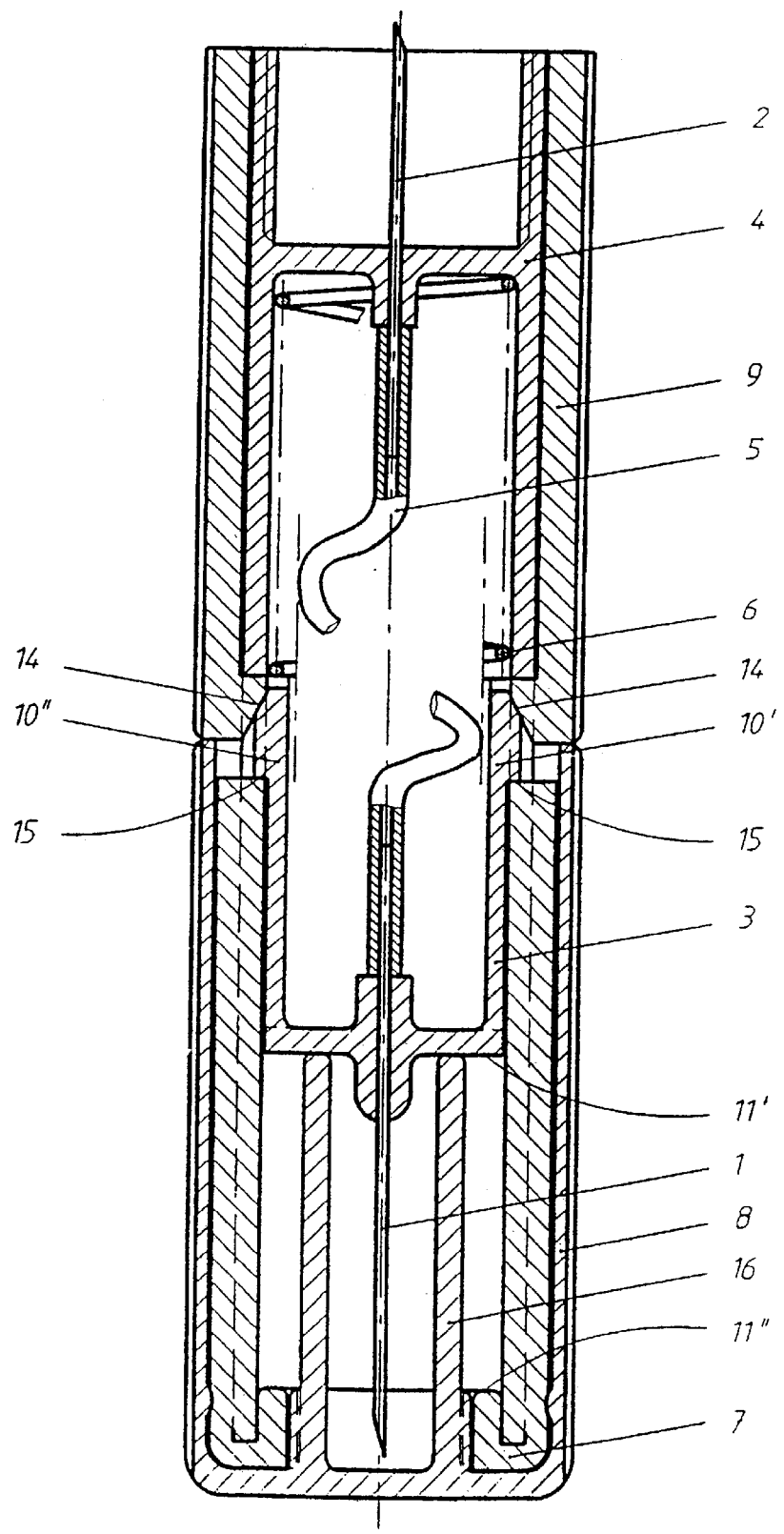
FIG. 1: is a longitudinal section through the device for introducing a needle in accordance with the invention, the device being in the starting position or resting position.

Referring now to FIG. 1, there is illustrated the device for introducing a needle in accordance with the invention for injecting a liquid substance. The device for introducing a needle can be coupled to the conventional injection device 12, for example, by a screw lock or by a latch cam mount (not shown). Via the piercing needle 2 provided at one end of the device for introducing a needle, the device for introducing a needle is connected to the pen cartridge 13 of the conventional injection device 12. Via the injection needle 1 provided at the other end of the device for introducing a needle, the liquid substance is injectable into the tissue skin or subcutaneously. Provided between the piercing needle 2 and the injection needle 1 is the flexible connection 5 for liquid substance transport. The procedure of introducing the injection needle 1 into the tissue skin or subcutaneously occurs automatically after manual activation of a control element in the form of the initiator sleeve 9 of the device for introducing a needle, after which, the liquid substance can be administered via the conventional injection device 12. The initiator sleeve 9 is arranged longitudinally shiftable on the piercing needle mount 4 mounting the piercing needle 2 and cooperates with the injection needle mount 3, likewise longitudinally shiftable in the piercing needle mount 4 and in the stopper sleeve 7, said injection needle mount 3 mounting the injection needle 1. Introduction of the injection needle 1 into the tissue skin or subcutaneously occurs after manual activation of the initiator sleeve 9 by means of the force of the spring 6, in that the injection needle mount 3 together with the injection needle 1 is automatically moved in the direction of the tissue skin. In this way, the spring 6 is supported at its one end by the fixed piercing needle mount 4 and moves by its other end the injection needle mount 3 including the injection needle 1 in the direction of the tissue skin into which the injection needle 1 is automatically introduced. The cooperation of the initiator sleeve 9 and the injection needle mount 3 in manual activation of the initiator sleeve 9 occurs via the bevel tapers 14 by which the injection needle mount 3 is squeezed diametrically to thus defeat the lock consisting of the stopper 15 of the stopper sleeve 7 and the mounting cams 10', 10" of the injection needle mount 3 and thereby enabling the spring 6 to develop its urging effect. After manual activation of the initiator sleeve 9, the injection needle mount 3 together with the injection needle 1 is automatically moved in the direction of the tissue skin by the force of the spring 6 until the face 11' of the injection needle mount 3 comes up against the face 11" of the stopper sleeve 7. On completion of injection, the injection needle mount 3 with the injection needle 1 can be shifted back manually by means of the safety cap 8 surrounding the stopper sleeve 7 against the force of the spring 6 until the lock comprising the stopper 15 of the stopper sleeve 7 and the mounting cams 10', 10" of the injection needle mount 3 is again effective. At the same time, the initiator sleeve 9 is longitudinally shifted by means of the bevel tapers 14 in the direction of the conventional injection device 12 by the safety cap 8 so that the initiator sleeve 9 is retracted into the starting position or resting position and is ready for a repeat manual activation. For retracting the injection needle mount 3 with the injection needle 1 by means of the safety cap 8, the latter is provided in its interior with a protective cylinder 16 surrounding the injection needle 1, this protective cylinder 16 having, for one thing, the function of protecting the injection needle 1 and, for another, the function of contacting by its open end the face 11' of the injection needle mount 3 and thus retracting the injection needle mount 3 together with the injection needle as well as the initiator sleeve 9 into the starting position when the safety cap 8 is shifted into the condition protecting the injection needle 1.

The functioning of the device for introducing a needle in accordance with the invention will now be described.

The device for introducing a needle is mechanically coupled to the conventional injection device 12 by e.g. a screw lock or by a latch cam mount or similar, the piercing needle 2 piercing the pen cartridge septum to ensure that the liquid substance to be injected communicates with the device for introducing a needle. The user then locates the device for introducing a needle to the preferred tissue skin location before then activating the initiator sleeve 9 by pushing it longitudinally down in the direction of the tissue skin until the lock consisting of the stopper 15 of the stopper sleeve 7 and the mounting cams 10', 10" of the injection needle mount 3 is defeated. This enables the spring 6 to develop its force and automatically urge the injection needle mount 3 with the injection needle 1 in the direction of the tissue skin until the face 11' of the injection needle mount 3 comes up against the face 11" of the stopper sleeve 7, as a result of which the injection needle 1 is automatically introduced into the tissue skin. Now, the user is able to deliver the dose of liquid substance to be administered by means of the conventional injection device 12. On completion of injection, the injection needle mount 3 with the injection needle 1 can be manually shifted back against the force of the spring 6 by means of the safety cap 8 surrounding the stopper sleeve 7. The lock is again effective and, at the same time, the initiator sleeve 9 returns to its starting position or resting position. The piercing needle mount 3 may be preferably slotted in the region of the bevel tapers 14 to improve its elasticity when it is squeezed in cooperating with the initiator sleeve 9 during activation to defeat the lock.

Figure 2:
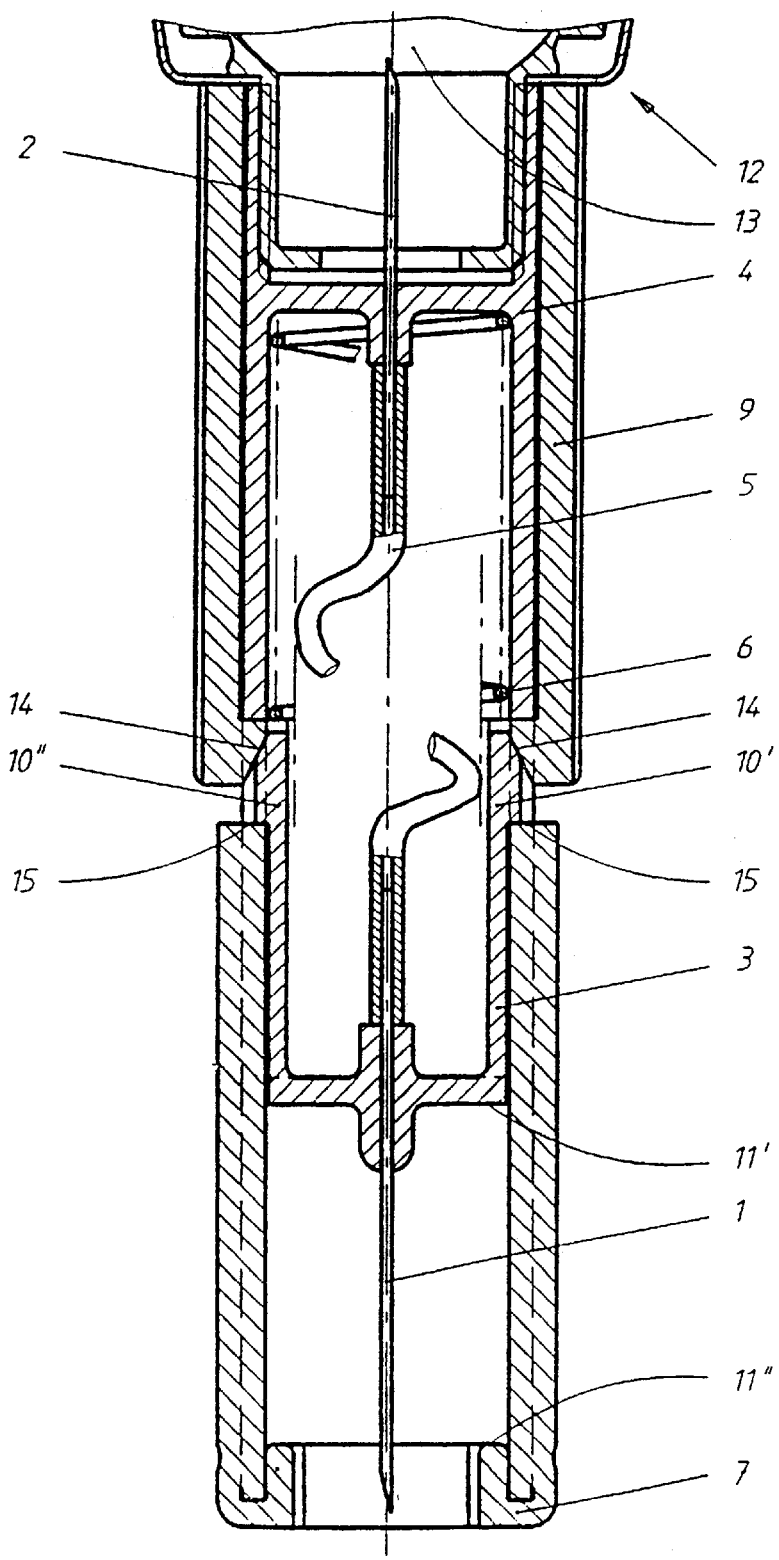
FIG. 2: is a longitudinal section through the device for introducing a needle in accordance with FIG. 1, the device being in the safety release position after removal of the safety cap.

Referring now to FIG. 2, there is illustrated a longitudinal section through the device for introducing a needle in the released condition after removal of the safety cap 8. Except for this safety cap 8, FIG. 2 is substantially identical to FIG. 1. The reference numerals are identical in both figures.

Figure 3:
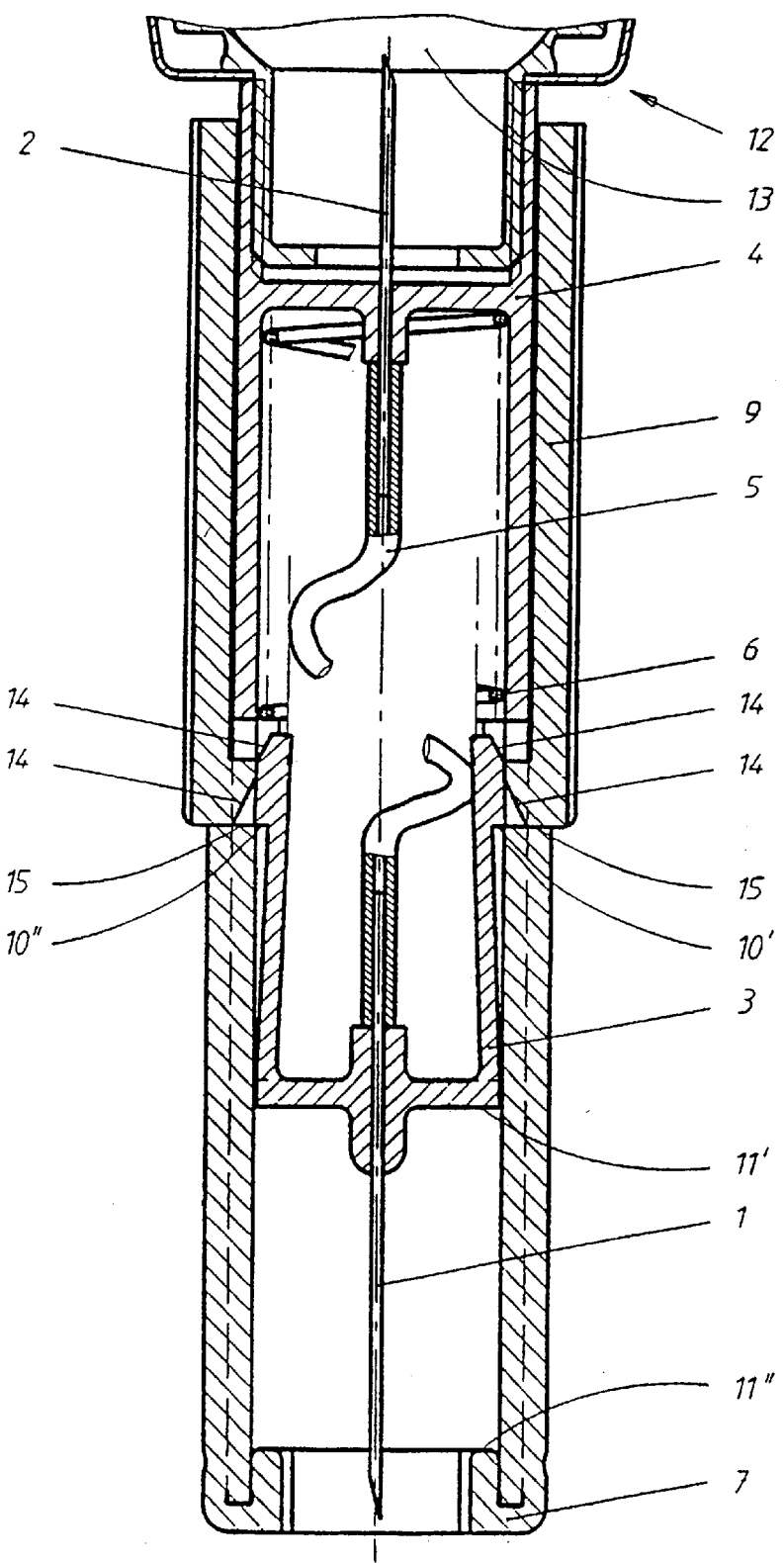
FIG. 3: is a longitudinal section through the device for introducing a needle after manual activation of the initiator sleeve.

FIG. 3 illustrates a longitudinal section through the device for introducing a needle after manual activation of the initiator sleeve 9. It is evident from this figure how, immediately after defeating the lock consisting of the stopper 15 of the stopper sleeve 7 and the mounting cams 10', 10" of the injection needle mount 3, due to cooperation of the bevel tapers 14 of the injection needle mount 3 and initiator sleeve 9, the injection needle mount 3 is flexibly squeezed so that the spring 6 can develop its force and automatic introduction of the injection needle 1 into the tissue skin or subcutaneously can commence.

The apparatus in accordance with the invention is applicable for administering medications preferably. However, it may also be used in all applications in which a liquid substance is to be introduced into a body and the injection needle is required to be inserted automatically.

In the foregoing description, a preferred embodiment of the invention has been presented for the purpose of illustration and description. It is not intended to be exhaustive or to limit the invention to the precise form disclosed. Obvious modifications or variations are possible in light of the above teachings. The embodiment was chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. A device for introducing a needle for injecting a liquid substance, said device comprising:
    a housing;
    a rear longitudinal part forming a portion of the housing and including a piercing needle, the rear longitudinal part being connectable to an injection device separate from the housing;
    a front longitudinal part forming another portion of the housing and including an injection needle for delivering said liquid; and
    a flexible connection between said piercing needle and said injection needle.

2. The device as set forth in claim 1, wherein said device is connectable via said piercing needle to said injection device, said liquid substance injectable into a user's tissue, skin or subcutaneously via said injection needle, and wherein the procedure of introducing said injection needle into the tissue, skin or subcutaneously occurs automatically following manual activation of a control element accommodated in said rear longitudinal part, said liquid substance thus being administered via said injection device.

3. The device as set forth in claim 2, wherein said control element is an initiator sleeve shiftable longitudinally on a piercing needle mount for mounting said piercing needle and cooperating with a likewise longitudinally shiftable injection needle mount for mounting said injection needle.

4. The device as set forth in claim 3, further comprising a spring, wherein the automatic introducing of said injection needle into the tissue, skin or subcutaneously is driven by the spring.

5. The device as set forth in claim 4, wherein said spring is supported at its one end by said piercing needle mount and at its other end by said injection needle mount.

6. The device as set forth in claim 3, wherein said cooperation of said initiator sleeve and said injection needle mount in the manual activation of said initiator sleeve occurs via bevel tapers by which said injection needle mount is squeezed diametrically thereby defeating a lock comprising a stopper and mounting cams associated with the injection needle mount such that said spring can develop its urging effect.

7. The device as set forth in claim 6, wherein, after manual activation of said initiator sleeve, said injection needle mount and injection needle automatically move toward said tissue or skin by said force of said spring until a face of said injection needle mount comes up against a face of a stopper sleeve.

8. The device as set forth in claim 7, wherein, upon completion of an injection, said injection needle mount and injection needle can be shifted back manually by means of a safety cap surrounding said stopper sleeve against said force of said spring until said lock is again effective and, at the same time, said initiator sleeve is longitudinally shiftable by means of said bevel tapers in the direction of said injection device, said initiator sleeve then ready for a repeated manual activation.

9. The device as set forth in claim 8, wherein said safety cap is provided in its interior with a protective cylinder surrounding said injection needle.

10. The device as set forth in claim 9, wherein it is suitable for administering medications.

11. The device as set forth in claim 1, wherein said flexible connection is an elongated tubular member suitable for transporting a liquid and is provided between said piercing needle and said injection needle.

12. A device for use with an injection device for automatically introducing into a user an injection needle for injecting a liquid substance, said device comprising:
   a housing;
   a rear longitudinal part forming a portion of the housing and carrying a piercing needle, the rear longitudinal part adapted for connection to the injection device that is separate from the housing;
   a front longitudinal part forming another portion of the housing and carrying the injection needle; and
   an elongated flexible connection disposed within the housing between the piercing needle and injection needle.

13. The device according to claim 12, further comprising a manually-operable control element associated with the rear longitudinal part, wherein, after operation of the control element, the introduction of the injection needle into said user occurs automatically.

14. A device for introducing a needle for injecting a liquid substance, said device comprising:
   a rear longitudinal part including a piercing needle, the rear longitudinal part being connectable to an injection device;
   a front longitudinal part biased for automated movement separate and independently from said piercing needle and including an injection needle for delivering said liquid; and
   a flexible connection between said piercing needle and said injection needle.

15. The device as set forth in claim 14, wherein said device is connectable via said piercing needle to said injection device, said liquid substance injectable into a user's tissue, skin or subcutaneously via said injection needle, and wherein the procedure of introducing said injection needle into the tissue, skin or subcutaneously occurs automatically by advancement of said injection needle separate from and relative to said piercing needle following manual activation of a control element accommodated in said rear longitudinal part, said liquid substance thus being administered via said injection device.

16. The device as set forth in claim 15, wherein said control element is an initiator sleeve shiftable longitudinally on a piercing needle mount for mounting said piercing needle and cooperating with a likewise longitudinally shiftable injection needle mount for mounting said injection needle.

17. The device as set forth in claim 16, further comprising a spring, wherein the automatic introducing of said injection needle into the tissue, skin or subcutaneously is driven by the spring.

18. The device as set forth in claim 17, wherein said spring is supported at its one end by said piercing needle mount and at its other end by said injection needle mount.

19. The device as set forth in claim 16, wherein said cooperation of said initiator sleeve and said injection needle mount in the manual activation of said initiator sleeve occurs via bevel tapers by which said injection needle mount is squeezed diametrically thereby defeating a lock comprising a stopper and mounting cams associated with the injection needle mount such that said spring can develop its urging effect.

20. The device as set forth in claim 19, wherein, after manual activation of said initiator sleeve, said injection needle mount and injection needle automatically move toward said tissue or skin by said force of said spring until a face of said injection needle mount comes up against a face of a stopper sleeve.

21. The device as set forth in claim 20, wherein, upon completion of an injection, said injection needle mount and injection needle can be shifted back manually by means of a safety cap surrounding said stopper sleeve against said force of said spring until said lock is again effective and, at the same time, said initiator sleeve is longitudinally shiftable by means of said bevel tapers in the direction of said injection device, said initiator sleeve then ready for a repeated manual activation.

22. The device as set forth in claim 14, wherein said flexible connection is an elongated tubular member suitable for transporting a liquid and is provided between said piercing needle and said injection needle.

* * * * *